US010307306B2

(12) United States Patent
Henderson

(10) Patent No.: US 10,307,306 B2
(45) Date of Patent: Jun. 4, 2019

(54) MALE INCONTINENCE WRAP SYSTEMS

(71) Applicant: Gilbert G. Henderson, Chicago, IL (US)

(72) Inventor: Gilbert G. Henderson, Chicago, IL (US)

( * ) Notice: Subject to any disclaimer, the term of this patent is extended or adjusted under 35 U.S.C. 154(b) by 0 days.

(21) Appl. No.: 15/730,482

(22) Filed: Oct. 11, 2017

(65) Prior Publication Data
US 2018/0028367 A1    Feb. 1, 2018

Related U.S. Application Data

(63) Continuation-in-part of application No. 14/295,099, filed on Jun. 3, 2014, now abandoned.

(60) Provisional application No. 61/830,921, filed on Jun. 4, 2013.

(51) Int. Cl.
| | | |
|---|---|---|
| *A61F 13/15* | (2006.01) |
| *A61F 13/471* | (2006.01) |
| *A61F 13/84* | (2006.01) |
| *A61F 13/531* | (2006.01) |
| *A61F 13/56* | (2006.01) |
| *A61F 13/64* | (2006.01) |
| *A61F 13/47* | (2006.01) |
| *A61F 13/475* | (2006.01) |
| *A61F 13/551* | (2006.01) |
| *A61F 13/58* | (2006.01) |
| *A61F 13/45* | (2006.01) |

(52) U.S. Cl.
CPC ........ *A61F 13/471* (2013.01); *A61F 13/4704* (2013.01); *A61F 13/475* (2013.01); *A61F 13/531* (2013.01); *A61F 13/551* (2013.01); *A61F 13/5611* (2013.01); *A61F 13/581* (2013.01); *A61F 13/64* (2013.01); *A61F 13/8405* (2013.01); *A61F 2013/15121* (2013.01); *A61F 2013/4568* (2013.01); *A61F 2013/8408* (2013.01)

(58) Field of Classification Search
CPC .......... A61F 5/451; A61F 5/453; A61F 5/581; A61F 13/471; A61F 13/581; A61F 2013/15121; A61F 2013/4512; A61F 2013/51078
USPC ........................................................ 604/349
See application file for complete search history.

(56) References Cited

U.S. PATENT DOCUMENTS

| | | | | |
|---|---|---|---|---|
| 2,612,164 A | * | 9/1952 | Miller | A61F 13/49004 604/398 |
| 4,576,599 A | * | 3/1986 | Lipner | A61F 5/4401 604/352 |
| 5,695,485 A | * | 12/1997 | Duperret | A61F 5/453 604/349 |

(Continued)

*Primary Examiner* — Jacqueline F Stephens
(74) *Attorney, Agent, or Firm* — RG Patent Consulting, LLC; Rachel Gilbay

(57) ABSTRACT

The male incontinence wrap system is a disposable absorbent pad designed to be wrapped around the male genital member of a person suffering from incontinence. The pad is wrapped around the male genital and secured by a first adhesive strip and then folded back at the end and held in place by a second adhesive strip, an elastic band, or both. An adhesive peel-and-stick strip attaches the absorbent pad assembly around the user to prevent sliding. At least one fold crease can be included extending between first and second edges and aids in the folding and forming of a pouch-shaped interior volume.

19 Claims, 10 Drawing Sheets

(56) References Cited

U.S. PATENT DOCUMENTS

| | | | | |
|---|---|---|---|---|
| 6,479,726 B1* | 11/2002 | Cole | ................ | A61F 13/471 |
| | | | | 604/317 |
| 2015/0328436 A1* | 11/2015 | Ahrony | ............. | A61M 25/02 |
| | | | | 604/544 |

* cited by examiner

MALE INCONTINENCE WRAP SYSTEMS

CROSS-REFERENCE TO RELATED APPLICATION

The present application is related to and claims priority from prior provisional application Ser. No. 61/830,921, filed Jun. 4, 2013, and utility application Ser. No. 14/295,099, filed Jun. 3, 2014, which applications are incorporated herein by reference.

COPYRIGHT NOTICE

A portion of the disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever. 37 CFR 1.71 (d).

BACKGROUND OF THE INVENTION

The following includes information that may be useful in understanding the present invention(s). It is not an admission that any of the information provided herein is prior art, or material, to the presently described or claimed inventions, or that any publication or document that is specifically or implicitly referenced is prior art.

1. Field of the Invention

The present invention relates generally to the field of male incontinence devices and more specifically relates to a male incontinence wrap system.

2. Description of the Related Art

Urinary incontinence (UI), involuntary urination, or enuresis is any involuntary leakage of urine. It can be a common and distressing problem, which may have a profound impact on quality of life. Urinary incontinence almost always results from an underlying treatable medical condition but is under-reported to medical practitioners. Urinary incontinence is especially prevalent in the elderly, which limits activities and traveling of the sufferer. Urinary incontinence in younger people poses many problems that can be in addition to what elderly do experience because of a developing social life.

Medical treatments for urinary incontinence can include drugs, exercise, and even surgery. In many cases, there just is nothing that can be done. The individual has to rely on devices already on the market. The most common is incontinence underwear. Unfortunately wearing incontinence underwear is bulky and is not unnoticeable when worn under the types of clothes that many of the younger people wear. Incontinence underwear is also not quickly or easily changed in public environments. A more easily concealed and undetectable solution is needed.

Various attempts have been made to solve the above-mentioned problems such as those found in U.S. Pat. No. 6,479,726 to Walter E. Cole, U.S. Pat. No. 4,064,880 to Dexter J. Logan; and U.S. Pub. No. 2008/0234642 to Frank V. Patterson et al. This art is representative of disposable male incontinence devices. None of the above inventions and patents, taken either singly or in combination, is seen to describe the invention as claimed.

Ideally, a disposable male incontinence device should provide comfort, be readily concealable, and cost effective using minimal material and, yet would operate reliably and be manufactured at a modest expense. Thus, a need exists for a reliable male incontinence wrap system to avoid the above-mentioned problems.

BRIEF SUMMARY OF THE INVENTION

In view of the foregoing disadvantages inherent in the known male incontinence device art, the present invention provides a novel male incontinence wrap system. The general purpose of the present invention, which will be described subsequently in greater detail, is to provide comfort, concealment, and cost effectiveness of manufacture by using minimal material.

The present invention, male incontinence wrap systems, as disclosed herein, preferably comprises an absorbent pad assembly comprising an absorbent pad having an inside surface, an outside surface, an absorbent layer, a first edge, a second edge, a proximate end, a distal end, an adhesive member, and at least one securing band.

The absorbent pad of the absorbent pad assembly is structured and arranged to wrap around a male genital member and to absorb an unintentionally released urinary fluid. The absorbent pad assembly is disposable and may comprise a hypoallergenic paper. The absorbent layer of the absorbent pad may comprise a paper element that is absorbent and expandable. The absorbent pad comprises a substantially rectangular shape in an unfolded condition.

The absorbent pad is defined and bound between the inside surface and the outside surface, the first edge and the second edge, and the proximate end and the distal end. The inside surface and the outside surface are parallel planar to each other, separated by and parallel planar with the absorbent layer. The outside surface of the absorbent pad is moisture impermeable. The inside surface of the absorbent pad is structured and arranged to allow moisture to pass therethrough to the absorbent layer while the inside surface remains substantially free from moisture. The first edge and the second edge are parallel planar to each other and located at opposing sides of the absorbent pad from each other and the proximate end is located at an opposite end of the absorbent pad from the distal end. The proximate end and the distal end are perpendicular planar to the first edge and the second edge.

The adhesive member is attached to the first edge or the second edge of the outside surface of the absorbent pad and may be a rectangular strip about 3 or 4 inches long. The adhesive member is constructed to be removably attached to the absorbent pad circumferentially to hold it in place. About 50% of the length of the adhesive member is non-removably attached to the first edge of the disposable pad and about 50% of the length is designed to be secured to the second edge with the absorbent pad wrapped around male genital member. The non-attached end of the adhesive member, before wearing the absorbent pad assembly, is preferably a peel-and-stick strip that can be removably attached back to the outside surface of the absorbent pad. The adhesive member is preferably an adhesive tape that is fast adhering and non-removable from the first edge or the second edge of the outside surface of the absorbent pad. Other securing means may be employed.

The absorbent pad is structured and arranged to wrap about the male genital member and to be secured in place via at least one securing band stretched about the circumference of a donned absorbent pad. The distal end of the absorbent pad assembly may comprise a second adhesive member for securing the distal end in a folded arrangement. The absorbent pad is able to be folded at the distal end after the absorbent pad is folded about the male genital member and secured via at least one securing band to prevent leakage.

The securing band(s) may comprise a rubber band but in some embodiments may comprise adhesive strips. The absorbent pad is rolled into a tubular shape when in a ready for use condition, with the distal end folded back and held by a securing band(s) wrapped around the circumference. The absorbent pad assembly is useful for collecting the urinary fluid from an incontinent user-wearer and preventing the collected urinary fluid from contacting the clothes of the user-wearer. The absorbent pad assembly comprises an anti-bacterial agent and is structured and arranged to prevent release of odors. The absorbent pad assembly is able to keep the user-wearer dry which is desirable to avoid uncomfortable or embarrassing situations from occurring.

A kit is embodied herein for the male incontinence wrap system preferably comprising a box having at least one absorbent pad assembly, and at least one set of user instructions.

In accordance with the embodiments of the present invention a preferred method of use is disclosed herein preferably comprising the steps of wrapping the left edge and the right edge of an absorbent pad assembly around a male genital member to encircle the member, securing via a first adhesive member, folding the distal end of the absorbent pad assembly back 180 degrees, securing the distal end of the folded absorbent pad assembly via a second adhesive member, securing the distal end of the folded absorbent pad assembly via at least one securing band, using the absorbent pad assembly, and removing and discarding the used absorbent pad assembly.

The present invention holds significant improvements and serves as a male incontinence wrap system. For purposes of summarizing the invention, certain aspects, advantages, and novel features of the invention have been described herein. It is to be understood that not necessarily all such advantages may be achieved in accordance with any one particular embodiment of the invention. Thus, the invention may be embodied or carried out in a manner that achieves or optimizes one advantage or group of advantages as taught herein without necessarily achieving other advantages as may be taught or suggested herein. The features of the invention which are believed to be novel are particularly pointed out and distinctly claimed in the concluding portion of the specification. These and other features, aspects, and advantages of the present invention will become better understood with reference to the following drawings and detailed description.

BRIEF DESCRIPTION OF THE DRAWINGS

The figures which accompany the written portion of this specification illustrate embodiments and method(s) of use for the present invention, male incontinence wrap systems, constructed and operative according to the teachings of the present invention.

The various embodiments of the present invention will hereinafter be described in conjunction with the appended drawings, wherein like designations denote like elements.

DETAILED DESCRIPTION

As discussed above, embodiments of the present invention relate to a male incontinence device and more particularly to a male incontinence wrap system as used to improve cost effectiveness and reduce material.

Generally speaking, the male incontinence wrap system is a disposable absorbent pad designed to be wrapped around the male genital member of a person suffering from incontinence. The pad is wrapped around the male genital member and then folded back at the distal end and then held in place by a second adhesive strip, an elastic band, or both. An adhesive peel-and-stick strip attaches the absorbent pad assembly around the user to prevent sliding.

Figure 1:
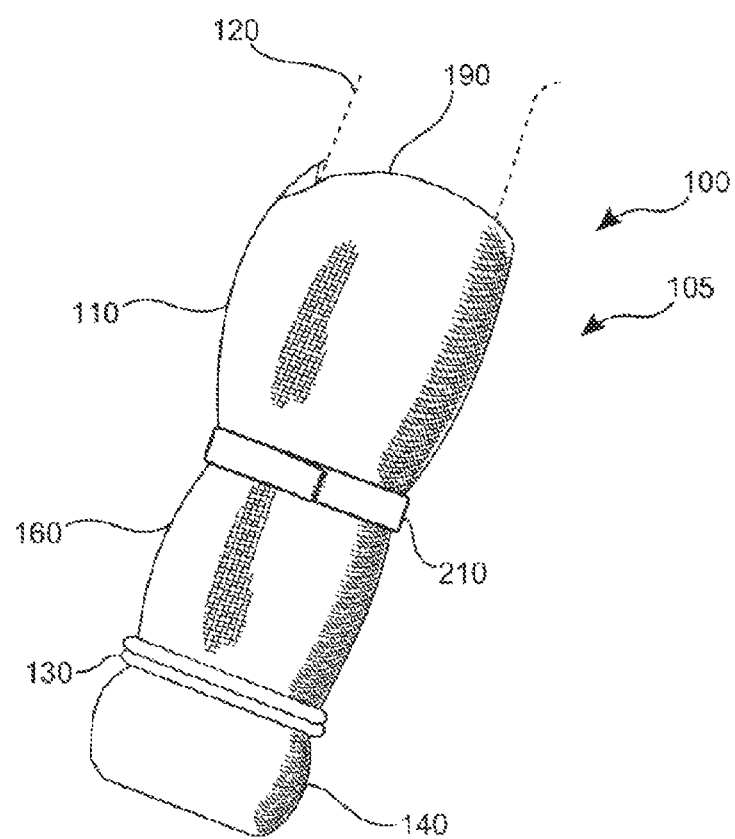
FIG. 1 shows a perspective view illustrating an as used condition of a male incontinence wrap system according to an embodiment of the present invention.

Referring to the drawings by numerals of reference there is shown in FIG. 1, a perspective view illustrating an as used condition of male incontinence wrap systems 100 according to an embodiment of the present invention.

Male incontinence wrap systems 100 is designed to provide a lined, absorbent, disposable wrap to be worn beneath the underclothes of males who suffer urinary incontinence. Discreet, effective, easily discarded and replaced, and designed to fully absorb and contain any urinary moisture released, the incontinence wrap for men would spare the user embarrassment, distress, discomfort and inconvenience and make the job of caregivers easy and efficient.

Absorbent pad 110 of absorbent pad assembly 105 is structured and arranged to wrap around male genital member 120 and to absorb an unintentionally released urinary fluid. Absorbent pad assembly 105 is disposable and may comprise a hypoallergenic paper. Securing band(s) 130 may comprise a rubber band but in some embodiments may comprise adhesive strips. Securing band(s) 130 are circumferentially placed around the wrapped absorbent pad 110 with distal end 199 folded back to prevent leakage.

Figure 2:
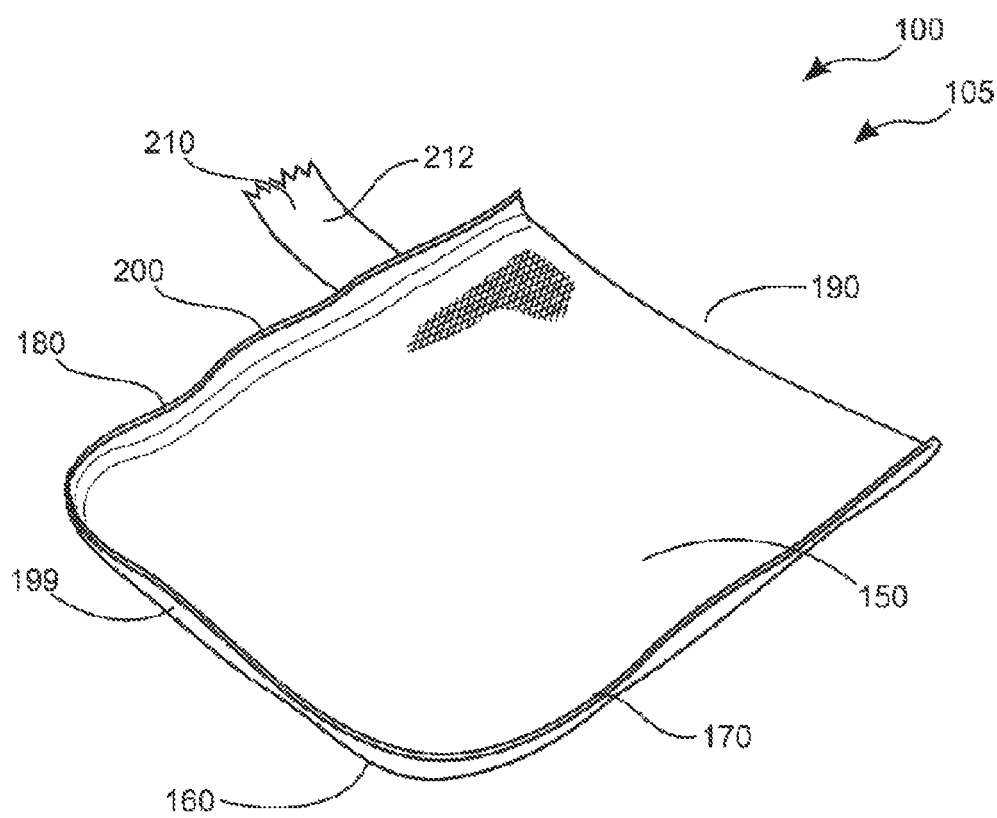
FIG. 2 is an inside perspective view illustrating the male incontinence wrap system according to an embodiment of the present invention of FIG. 1.

Referring now to FIG. 2, an inside perspective view illustrating male incontinence wrap systems 100 according to an embodiment of the present invention of FIG. 1.

Absorbent pad 110 is defined and bound between inside surface 150 and outside surface 160, first edge 170 and second edge 180, and proximate end 190 and distal end 199. Male incontinence wrap systems 100 preferably comprises absorbent pad assembly 105 having absorbent pad 110 with inside surface 150, outside surface 160, absorbent layer 200, first edge 170, second edge 180, proximate end 190, distal end 199, adhesive member 210, and at least one securing band(s) 130. About 50% of adhesive member 210 is preferably a peel-and-stick strip.

Adhesive member 210 is attached to first edge 170 or second edge 180 of outside surface 160 of absorbent pad 110 and may be a rectangular strip about 3 or 4 inches long. Adhesive member 210 is constructed to be removably attached to first edge 170 or second edge 180 and absorbent pad 110 wrapped circumferentially around male genital member 120 and the free end of adhesive member 210 attached back to outside surface 160 of absorbent pad 110. About 50% of the length of adhesive member 210 is non-removably attached to first edge of absorbent pad 110 and about 50% of the length is designed to be wrapped around absorbent pad assembly 105, closer to proximate end 199.

Figure 3:
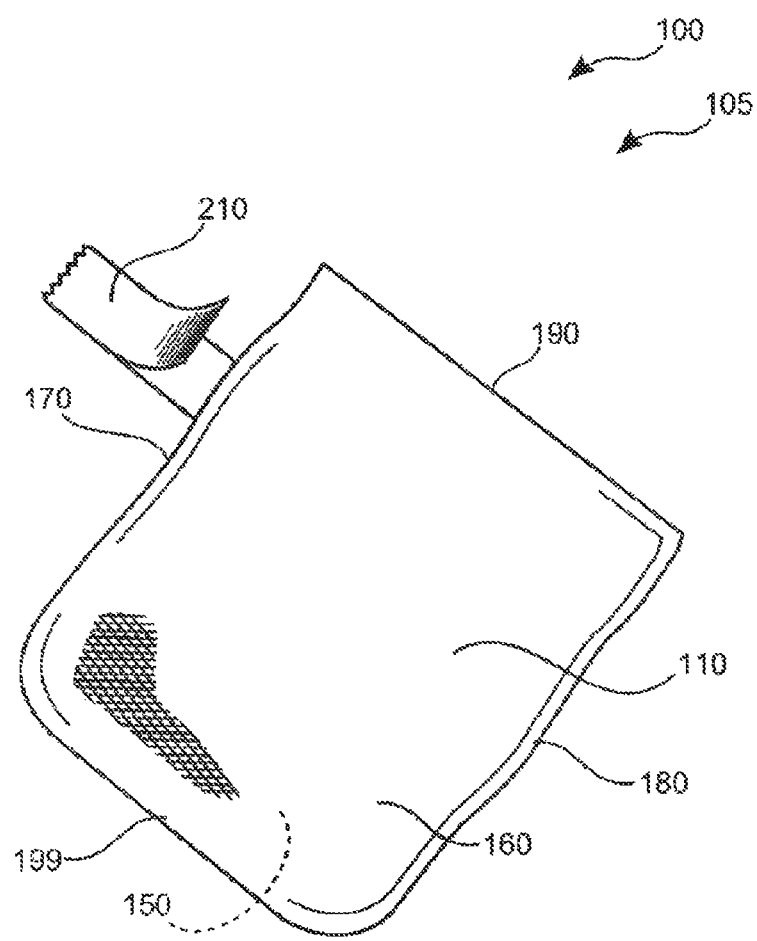
FIG. 3 is an outside perspective view illustrating the male incontinence wrap system according to an embodiment of the present invention of FIG. 1.

Referring now to FIG. 3, an outside perspective view illustrating male incontinence wrap systems 100 according to an embodiment of the present invention of FIG. 1.

Inside surface 150 and outside surface 160 are parallel planar to each other, separated by and parallel planar with absorbent layer 200. Outside surface 160 of absorbent pad 110 is moisture impermeable. Inside surface 150 of absorbent pad 110 is structured and arranged to allow moisture to pass through to absorbent layer 200 while inside surface contacting skin remains substantially free from moisture. First edge 170 and second edge 180 are parallel planar to each other and located at opposing sides of absorbent pad 110 from each other and proximate end 190 is located at an opposite end of absorbent pad 110 from distal end 199. Proximate end 190 and distal end 199 are perpendicular planar to first edge 170 and second edge 180. Absorbent pad assembly 105 is useful for collecting urinary fluid from an incontinent user-wearer and preventing urinary fluid from contacting the clothes of user-wearer. Absorbent pad assembly 105 may comprise an anti-bacterial agent and is structured and arranged to prevent release of odors. Absorbent pad assembly 105 is able to keep the user-wearer comfortable and dry.

Figure 4:
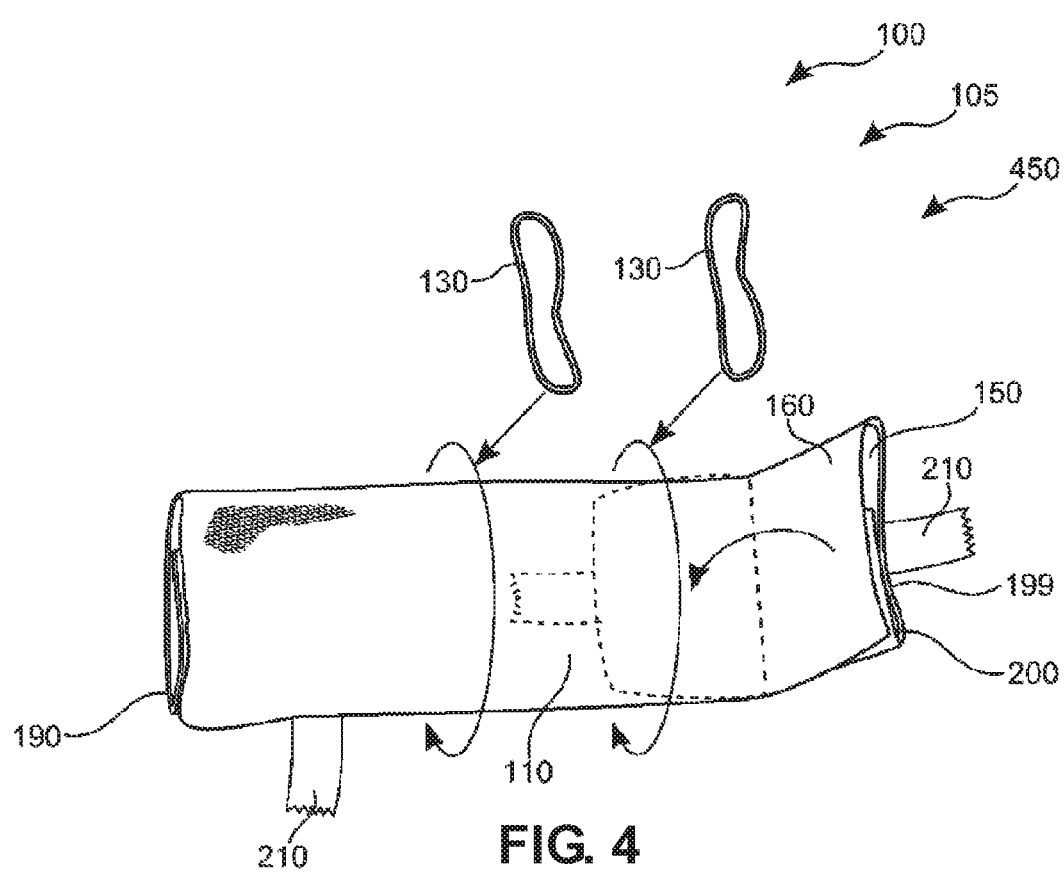
FIG. 4 is a folded perspective view illustrating male incontinence wrap system according to an embodiment of the present invention of FIG. 1.

Referring now to FIG. 4, showing a folded perspective view illustrating male incontinence wrap systems 100 according to an embodiment of the present invention of FIG. 1.

Adhesive member 210 is preferably a suitable adhesive tape that is fast adhering to and non-removable from first edge 170 or second edge 180 of outside surface 160 of absorbent pad 110. Absorbent pad 110 is structured and arranged to wrap about male genital member 120 and to be secured in place with at least one securing band(s) 130 and one adhesive member 210 stretched about the circumference of a donned absorbent pad 110. Distal end 199 of absorbent pad assembly 105 may comprise a second adhesive member 210 for securing distal end 199 in a folded arrangement with securing band(s) 130 providing additional securing. Absorbent pad 110 is able to be folded at distal end 199 after absorbent pad 110 is folded about male genital member 120 and secured via at least one securing band(s) 130 to prevent leakage. Absorbent pad 110 is rolled into a tubular shape when in a ready for use condition, with distal end 199 folded back and held by securing band(s) 130 and/or adhesive member 210 wrapped around the circumference.

Male incontinence wrap systems 100 may be sold as kit 450 comprising the following parts: at least one box (package, covered pouch or other suitable covering means) having at least one absorbent pad assembly 105; and at least one set of user instructions. The kit has instructions such that functional relationships are detailed in relation to the structure of the invention (such that the invention can be used, maintained, or the like in a preferred manner). Male incontinence wrap systems 100 may be manufactured and provided for sale in a wide variety of sizes and shapes for a wide assortment of applications. Upon reading this specification, it should be appreciated that, under appropriate circumstances, considering such issues as design preference, user preferences, marketing preferences, cost, structural requirements, available materials, technological advances, etc., other kit contents or arrangements such as, for example, including more or less components, customized parts, different wrap combinations, parts may be sold separately, etc., may be sufficient.

Figure 5:
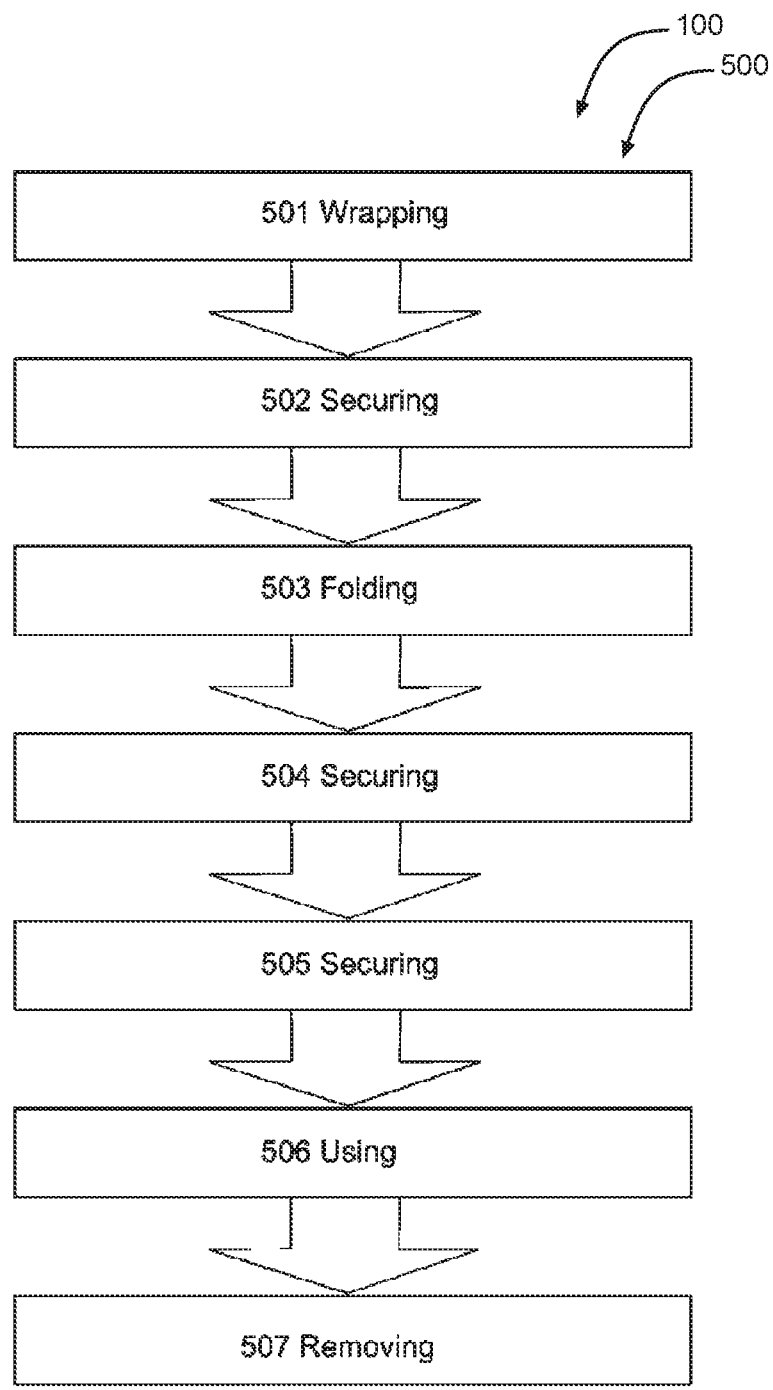
FIG. 5 is a flowchart illustrating a method of use for the male incontinence wrap system according to an embodiment of the present invention of FIGS. 1-4.
Figure 6:
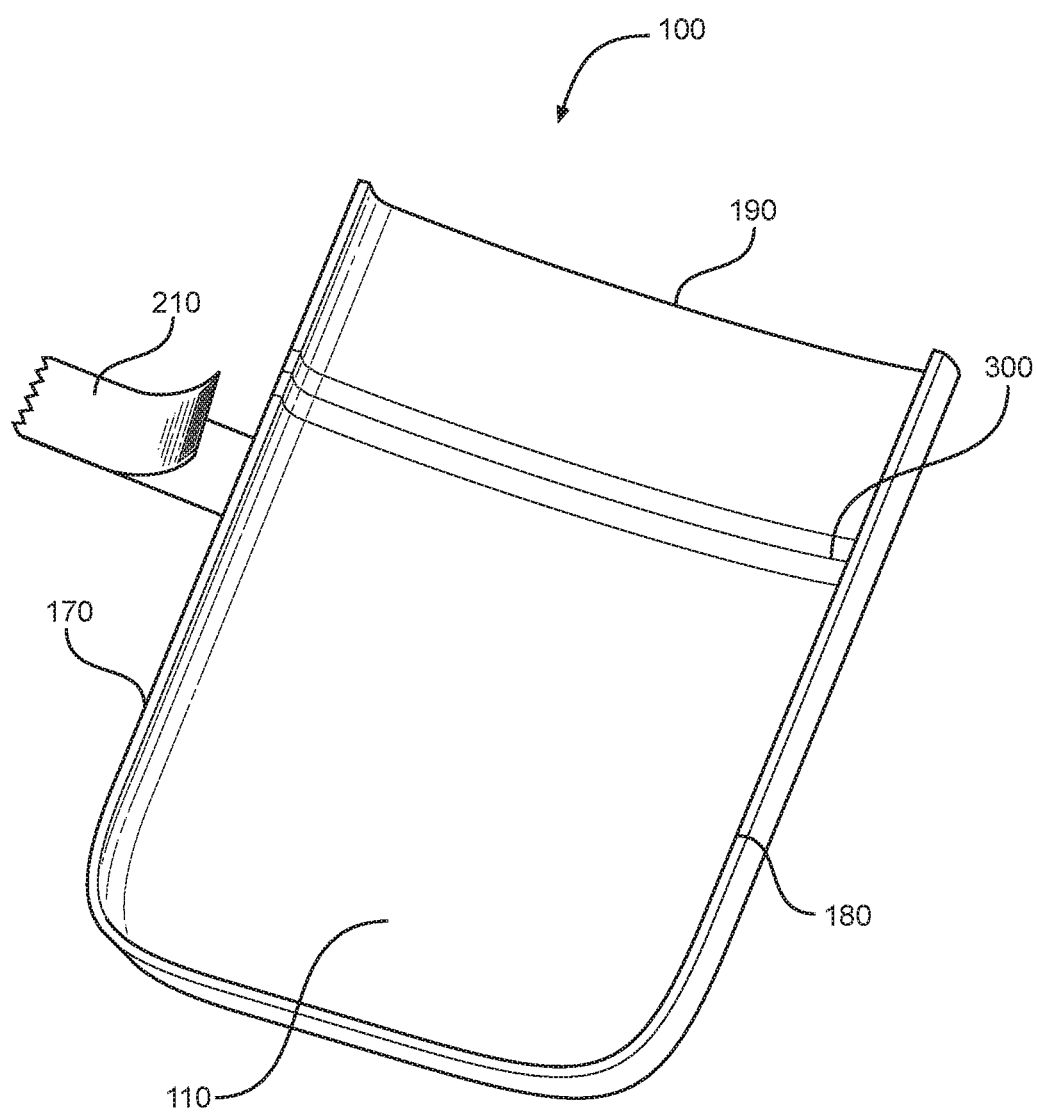
FIG. 6 is a perspective view illustrating the male incontinence wrap system of FIG. 1 further including an elongated fold crease formed as a scored depression extending between the first and second edges of the absorbent pad.

Referring now to FIG. 5, showing method of use 500 for male incontinence wrap systems 100.

A method of using (method of use 500) male incontinence wrap systems 100 may comprise the steps of step one 501 wrapping first edge 170 and second edge 180 of absorbent pad assembly 105 around male genital member 120 to encircle male genital member 120; step two 502 securing absorbent pad 110 via a first adhesive member 210; step three 503 folding distal end 199 of absorbent pad assembly 105 back 180 degrees; step four 504 securing distal end 199 of the folded absorbent pad assembly 105 via a second adhesive member 210; step five 505 securing distal end 199 of the folded absorbent pad assembly 105 via at least one securing band(s) 130 and/or one adhesive member 210; step six 506 using absorbent pad assembly 105; and step seven 507 removing and discarding the used absorbent pad assembly 105.

It should be noted that step 503 and 504 are optional steps and may not be implemented in all cases. Optional steps of method 500 are illustrated using dotted lines in FIG. 5 so as to distinguish them from the other steps of method 500.

As illustrated in FIGS. 6-10, an alternate embodiment of the disposable male incontinence wrap system includes a permanent and elongated fold crease 300 formed perpendicular to the first and second edges (170 and 180) that extends from the first edge to the second edge, and is adapted such that when the absorbent pad is folded and in use the absorbent pad is capable of being folded in a perpendicular fashion with respect to the first edge and the second edge thereby forming the pouch-shaped interior volume illustrated in FIG. 4. The permanent and elongated fold crease 300 may be formed as a scored depression extending along the length of the permanent and elongated fold crease between the first and second edges. The scored depression may be formed as a heat sealed depression.

Figure 7:
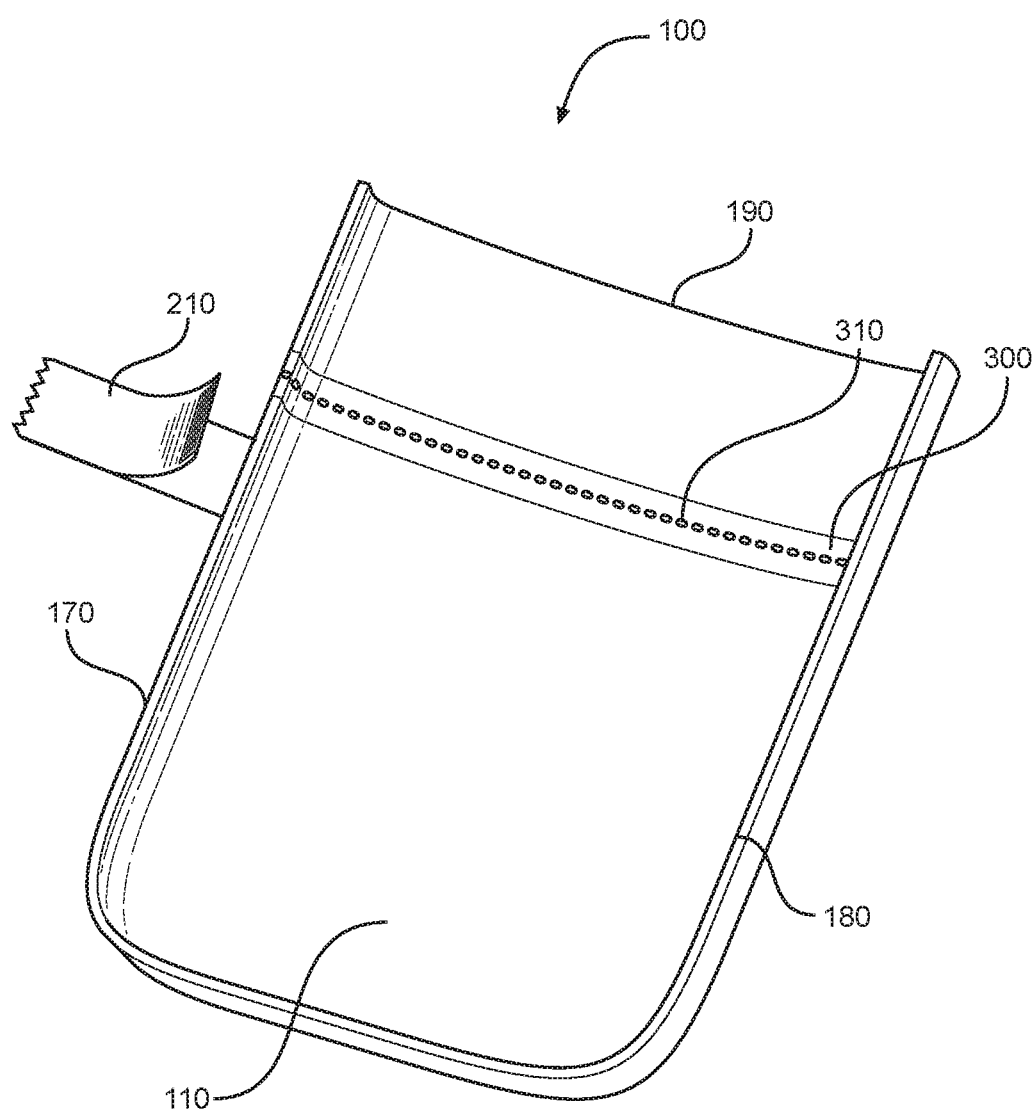
FIG. 7 is a perspective view illustrating the male incontinence wrap system of FIG. 1 wherein the elongated fold crease is formed including a series of spaced perforations between the first and second edges of the absorbent pad.

As illustrated in FIG. 7, the permanent and elongated fold crease 300 may be formed including a series of spaced perforations 320 extending along the length of the permanent and elongated fold crease between the first and second edges.

Figure 8:
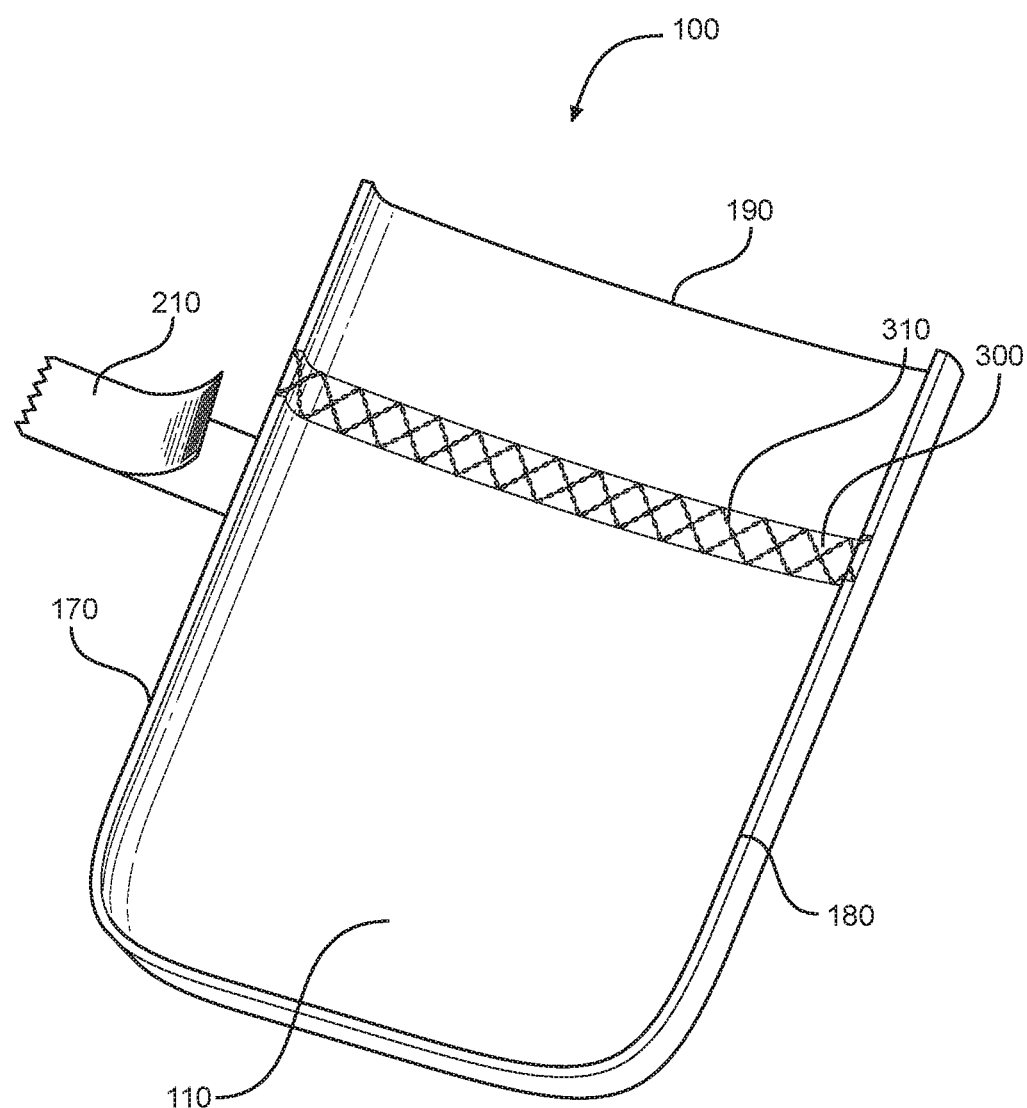
FIG. 8 is a perspective view illustrating the male incontinence wrap system of FIG. 1 wherein the elongated fold crease is formed including a threading material embossed into said absorbent pad between the first and second edges of the absorbent pad.

As illustrated in FIG. 8, the permanent and elongated fold crease 300 may include a threading material 310 embossed into the absorbent pad extending along the length of the permanent and elongated fold crease between the first and second edges.

Figure 9:
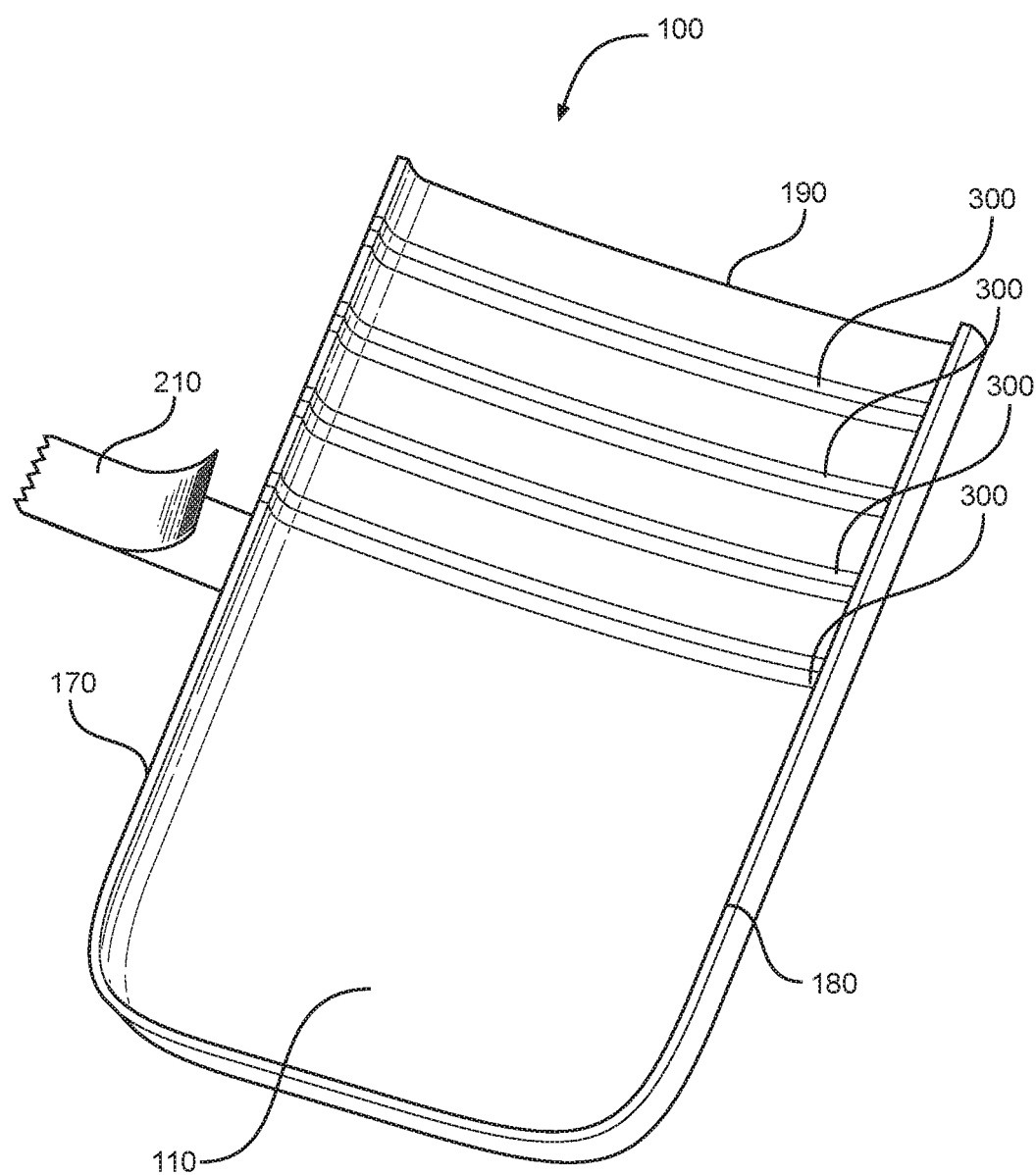
FIG. 9 is an inside perspective view illustrating the male incontinence wrap system of FIG. 1 wherein there are a plurality of spaced parallel permanent and elongated fold creases between the first and second edge of the absorbent pad.

As illustrated in FIG. 9, there also can be a plurality of spaced parallel permanent and elongated fold creases 300 between the first and second edges adapted and spaced such that the absorbent pad is capable of forming different sized pouch-shaped interior volumes.

Figure 10:
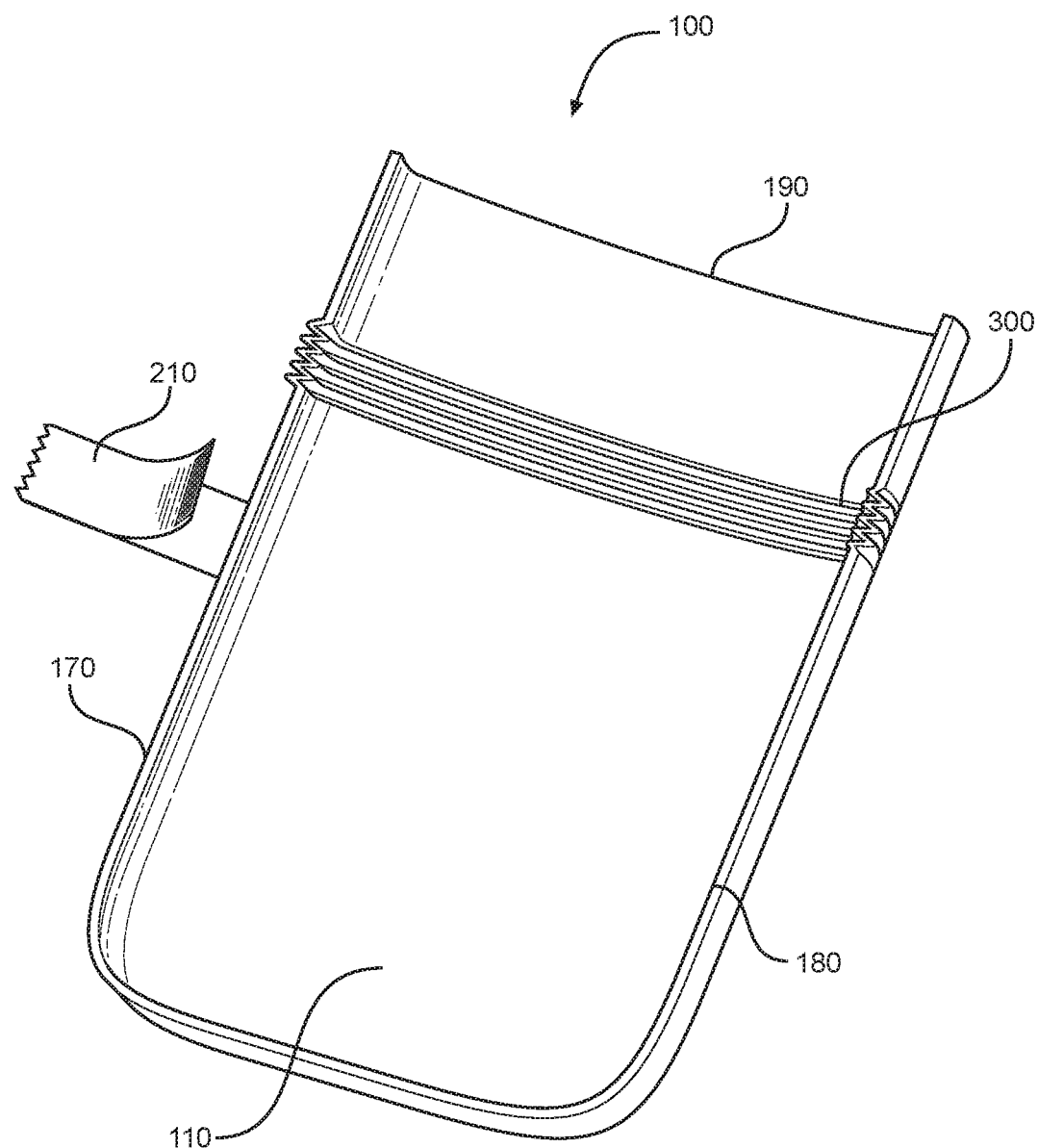
FIG. 10 is an inside perspective view illustrating the male incontinence wrap system of FIG. 1 wherein the permanent and elongated fold crease is formed from a flexible material.

As illustrated in FIG. 10, the permanent and elongated fold crease 300 may be formed from a flexible material adapted to expand the size of the pouch-shaped interior volume.

It should be noted that the steps described in the method of use can be carried out in many different orders according to user preference. The use of "step of" should not be interpreted as "step for", in the claims herein and is not intended to invoke the provisions of 35 U.S.C. § 112, ¶ 6. Upon reading this specification, it should be appreciated that, under appropriate circumstances, considering such issues as design preference, user preferences, marketing preferences, cost, structural requirements, available materials, technological advances, etc., other methods of use arrangements such as, for example, different orders within above-mentioned list, elimination or addition of certain steps, including or excluding certain maintenance steps, etc., may be sufficient.

The embodiments of the invention described herein are exemplary and numerous modifications, variations and rearrangements can be readily envisioned to achieve substantially equivalent results, all of which are intended to be embraced within the spirit and scope of the invention. Further, the purpose of the foregoing abstract is to enable the U.S. Patent and Trademark Office and the public generally, and especially the scientist, engineers and practitioners in the art who are not familiar with patent or legal terms or phraseology, to determine quickly from a cursory inspection the nature and essence of the technical disclosure of the application.

What is claimed:

1. A disposable male incontinence wrap system comprising:
    an absorbent pad assembly comprising;
        an absorbent pad having;
            an inside surface;
            an outside surface;
            an absorbent layer;
            a first edge;
            a second edge parallel to said first edge;
            a proximate end;
            a distal end;
            an adhesive member;
            at least one securing band; and
            a plurality of spaced parallel permanent and elongated fold creases formed perpendicular to said first and second edges and extending from said first edge to said second edge, and adapted such that said absorbent pad is adapted to be folded along any one of said plurality of spaced parallel permanent and elongated fold creases to thereby form pouch-shaped interior volumes of differing sizes;
        wherein said absorbent pad of said absorbent pad assembly is structured and arranged to wrap around a male genital member and to absorb an unintentionally released urinary fluid;
        wherein said absorbent pad is defined and bound between said inside surface and said outside surface, said first edge and said second edge, and said proximate end and said distal end;
        wherein said inside surface and said outside surface are parallel planar to each other, separated by and parallel planar with said absorbent layer;
        wherein said first edge and said second edge are parallel planar to each other and located at opposing sides of said absorbent pad from each other;
        wherein said proximate end is located at an opposite end of said absorbent pad from said distal end;
        wherein said proximate end and said distal end are parallel planar to said first edge and said second edge;
        wherein said adhesive member is attached to said proximate end of said outside surface of said absorbent pad;
        wherein said adhesive member is structured and arranged to removably attach said absorbent pad circumferentially about said male genital member and to be secured in place via said at least one securing band stretched about a circumference of a donned said absorbent pad;
        wherein said absorbent pad assembly is useful for collecting said urinary fluid from an incontinent said user-wearer and preventing said collected urinary fluid from contacting a clothes of said user-wearer;
        wherein said inside surface of said absorbent pad is structured and arranged to allow moisture to pass therethrough to said absorbent layer while said inside surface remains substantially free from moisture; and
        wherein said absorbent pad is adapted to be and is capable of being folded via any one of said plurality of spaced parallel permanent and elongated fold creases after said absorbent pad is folded about said male genital member and secured via said at least one securing band to prevent leakage.

2. The disposable male incontinence wrap system of claim 1 wherein said absorbent layer of said absorbent pad comprises a paper element that is absorbent and expandable.

3. The disposable male incontinence wrap system of claim 1 wherein said outside surface of said absorbent pad is moisture impermeable.

4. The disposable male incontinence wrap system of claim 1 wherein said adhesive member comprises adhesive tape, said adhesive tape non-removable from said proximate end of said outside surface of said absorbent pad.

5. The disposable male incontinence wrap system of claim 1 wherein said at least one securing band comprises a rubber band.

6. The disposable male incontinence wrap system of claim 1 wherein said absorbent pad comprises a substantially rectangular shape in an unfolded condition.

7. The disposable male incontinence wrap system of claim 6 wherein said absorbent pad comprises a hypoallergenic paper.

8. The disposable male incontinence wrap system of claim 7 wherein said absorbent pad assembly comprises an antibacterial agent and is structured and arranged to prevent release of odors.

9. The disposable male incontinence wrap system of claim 1 wherein said adhesive member comprises a rectangular strip about 3 inches long.

10. The disposable male incontinence wrap system of claim 9 wherein said adhesive member comprises about 50% of a length non-removably attached to said disposable pad and about 50% of said length that is able to be removably attached to said second edge.

11. The disposable male incontinence wrap system of claim 1 wherein the about 50% of said length of said adhesive member that is able to be removably attached to said second edge of said adhesive member comprises a peel-and-stick strip.

12. The disposable male incontinence wrap system of claim 1 wherein said absorbent pad comprises a tubular shape when in a ready for use condition.

13. The disposable male incontinence wrap system of claim 1 wherein said distal end of said absorbent pad assembly comprises a second adhesive member for securing said distal end in a folded arrangement.

14. The disposable male incontinence wrap system of claim 1 further comprising a kit including:
- a box comprising at least one said absorbent pad assembly; and
- at least one set of user instructions.

15. The disposable male incontinence wrap system of claim 1, wherein each of said plurality of permanent and elongated fold creases is formed including a series of spaced perforations extending along the length of said permanent and elongated fold crease between said first and second edges.

16. The disposable male incontinence wrap system of claim 1, wherein each of said plurality of permanent and elongated fold creases is formed as a scored depression extending along the length of said permanent and elongated fold crease between said first and second edges.

17. The disposable male incontinence wrap system of claim 16, wherein each said scored depression is formed as a heat sealed depression.

18. The disposable male incontinence wrap system of claim 1, wherein each of said plurality of permanent and elongated fold creases includes a threading material embossed into said absorbent pad extending along the length of said permanent and elongated fold crease between said first and second edges.

19. The disposable male incontinence wrap system of claim 1, wherein each of said plurality of permanent and elongated fold creases is formed from a flexible material adapted to expand the size of said pouch-shaped interior volume.

* * * * *